United States Patent [19]

Drachev et al.

[11] Patent Number: 5,642,195
[45] Date of Patent: Jun. 24, 1997

[54] DISPERSION INTERFEROMETER USING ORTHOGONALLY POLARIZED WAVES

[76] Inventors: Vladimir Prokopievich Drachev, ulitsa Ivanova, 30a, kv, 7; Sergei Alexeevich Babin, ulitsa Tereshkovoi, 34, kv.18, both of Novosibirsk, Russian Federation; Abdelmounaime Faousi Zerrouk, 147B Danbury Road, Oxford, United Kingdom, OX2 7AN

[21] Appl. No.: 290,956
[22] PCT Filed: Dec. 25, 1992
[86] PCT No.: PCT/RU92/00253
  § 371 Date: Feb. 28, 1995
  § 102(e) Date: Feb. 28, 1995
[87] PCT Pub. No.: WO94/15195
  PCT Pub. Date: Jul. 7, 1994
[51] Int. Cl.$^6$ ...................... G01B 9/02
[52] U.S. Cl. .............. 356/351; 356/349; 356/361
[58] Field of Search ...................... 356/345, 349, 356/351, 361, 358

[56] References Cited

U.S. PATENT DOCUMENTS 5,037,202  8/1991  Batchelder et al. ............ 356/349
5,394,240  2/1995  Matsumoto ..................... 356/349

FOREIGN PATENT DOCUMENTS 330380    11/1972  U.S.S.R. .
864942    9/1981   U.S.S.R. .
1673925   8/1991   U.S.S.R. .
2210973   6/1989   United Kingdom .

OTHER PUBLICATIONS

Pyatnitskii, L.N., et al., "Sensitive Three–Frequency Laser Interferometer", PTE, 1983, No. 5, pp. 181–18, with translation.

Primary Examiner—Frank Gonzalez
Assistant Examiner—Robert Kim
Attorney, Agent, or Firm—Keck, Mahin & Cate

[57] ABSTRACT

The invention relates to dispersion interferometers for measuring a dispersion portion of the refractive index of an investigated medium by an interferometric method and can be used in the optical industry and in the composition of diagnostic complexes of various plasma installations of the type of Tokamak, Stellarator, gas-discharge lasers. The dispersion interferometer comprising a radiation source, two nonlinear optical doublers of frequency at a distance ensuring a location of an object under examination therebetween, a light filter means and a recording device, all arranged along an optical axis. Additionally provided is a polarization beam splitter, and the two non-linear optical frequency doublers are so oriented that the directions of polarization of fast waves are orthogonal to each other and do not coincide with ones separated by the beam splitter and the radiation source.

6 Claims, 3 Drawing Sheets

DISPERSION INTERFEROMETER USING ORTHOGONALLY POLARIZED WAVES

TECHNICAL FIELD

The invention relates to dispersion interferometers of the type used for measuring the dispersion part of a refractive index of media under examination by an interferometric method and can be used in the optical industry and also in the composition of diagnostic complexes of various plasma installations of the type of Tokamak, Stallarator, gas discharge lasers.

PRIOR ART

The methods of interferometry make it possible to determine a change, necessitated by media, in the optical length of a path nS (n—refractive index, S—geometric length of the path). Given the length of the object under examination, one may conclude about the refractive index of a material and vice versa for objects with a known refractive index one can register the profile of its thickness with an accuracy comparable with the wavelength of radiation. If measurements are carried out on two different wavelengths $\lambda_1$ and $\lambda_2$, one can determine the dispersion portion of the optical length of the path $[n_1(\lambda_1)-n_2(\lambda_2)]S$. For example, in plasma the value of $(n_1-n_2)$ is unambiguously associated with electron concentration. The common feature of interferometers is the provision of two independent optical branches. The result of interference depends on the difference of wave phases travelling along two branches and converged in an interference element. Inasmuch as the wave phase in media depends on the geometric path, polarization and radiation frequency, we can single out three types of interference circuits. In classic interferometers practised on a large scale, the radiation of a source is divided into two waves with equal frequency, which travel on different geometric paths in the branches.

Very popular are interferometers for plasma diagnostics operating simultaneously on two and more wavelengths which are constructed according to the classical circuits of the first type, say, of Mach-Zender, Michelson, to mention only a few (L. N. Pyatnitsky, S. L. Rak, V. A. Ron'kin, G. C. Yakushev "Three-frequency high-responsive laser interferometer", PTE, 1983, N 5, pp. 181–185). The difference of geometric paths is a main reason behind the defect of such circuits—high response to the vibration of optical elements. For elimination of a vibration effect, a complex of measures are taken which complicate these systems, say, use of vibration-insulating bed plates, long wave radiations (inclusive of 337 µm), two-wavelength interferometers with a compensation of vibrations on a shorter wavelength (for instance, 0.63 µm).

Known in the art is also a new type of interferometers called dispersion of which two branches correspond to waves with a different frequency with the same geometric path (SU—PS 864942, O OID 9/02). They display a number of substantive advantages: first, a dispersion contribution is measured therein into a refractive index (in plasma it is determined by electrons), and is not derived as a difference of two large values; second, they possess a lesser response to the spurious vibrations of optical elements.

The dispersion interferometer of this type comprises a radiation source with a frequency $\omega$, two non-linear optical doublers of frequency at a distance providing the arrangement of an object under examination therebetween, a light filter and a register, means all located along the optical axis.

In this device, given the illumination of an interferometer with laser radiation with a frequency $\omega_1$, part of this radiation is converted into harmonic radiation with a frequency $\omega_2=2\omega_1$ in the first non-linear element. Thus, the object under examination is translucent with two wavelengths of the frequency $\omega_1$ and $\omega_2$. When passing through the second non-linear element the frequency $\omega_1$ is partially converted into a wave $\lambda'_r$ with the frequency $\omega_2$. A light filter cuts off the radiation of the fundamental frequency. At the output of the interferometer there remain two wavelengths—$\lambda_2$ and $\lambda'_r$ of harmonic radiation one of which ($\lambda_2$) is converted from $\omega_1$ prior to passage through the object, and the second one ($\lambda'_r$)—upon passage therethrough. The picture of interference of these two waves is registered in the image plane of the object formed by the lens.

Possible is a variant of an interferometer, according to which after the first non-linear element, at a distance providing a location of the object under examination perpendicular to the optical axis, provision is made of a flat mirror, in which case radiation with the frequency $\omega_1$ illuminating the interferometer is partially converted into a radiation with the frequency $\omega_2=2\omega_1$ at a first passage through the frequency doubler. The object is rayed with two waves $\lambda_1$ and $\lambda_2$ with the frequencies $\omega_1$ and $\omega_2$. This being so, each of these waves travels for the second time, as a result of reflection from the mirror, through the investigated object and the frequency doubler; on repeated passage through the doubler, the wave $\lambda_1$ with $\omega_1$ is converted into $\lambda'_r$ with $\omega_2$. After reflection from the semitransparent mirror, the fundamental frequency radiation is cut off by the filter. In the image plane of the object formed by the lens there is registered the pattern of interference of waves $\lambda_2$ and $\lambda'_r$. It is common knowledge that the relationship of the general intensity of interfering waves to their difference of phases $\psi=2\phi_1-\phi_2$ is as follows:

$$J = J_1 + J_2 + 2\sqrt{J_1 J_2}\ \cos\psi \qquad (1)$$

wherein $J_1$, $J_2$ intensities and $2\phi_1(\omega_1)$, $\phi_2(2\omega_2)$—wave phases of the second harmonic $\lambda_2$ and $\lambda'_r$, respectively. For the determination of the absolute values of measured phase shift, use is made of (I) according to which, the distance between the maxima of the interference pattern corresponds to $2\pi$.

In a similar way, operation is performed in photoelectrical recording, or the ratio $$\left(\frac{dJ}{d\psi}\right)_{max} : (J\max - J\min) = 1.$$

The above-described device is actually a non-linear dispersion interferometer. Non-linearity of the device leads to the ambiguous interpretation of recording results and, as a consequence low accuracy. In the second frequency doubler there occurs, depending on the value of $\psi=2\phi_1-\phi_2$, either conversion of fundamental radiation into the second harmonic or the reverse process of conversion of the second harmonic into a subharmonic. In general, a dependence $J(\psi)$ may be rather complex and not coinciding with the formula (1). This is due to a change in a dispersion difference of phases in the process of conversion. A kind of dependence is determined by the intensity of probe radiation power and also by the length and non-linear susceptibility of the frequency doubler.

Let us illustrate this assertion by the numerical solution of a set of equations for producing the second harmonic with arbitrary initial conditions.

The equations describing a change in amplitudes $\rho_j$ and phases $\phi_j$ of the waves:

$$E_j = Re[\bar{e}_j A_j(Z) \exp[i(k_j \cdot Z - jwt)]], \; j=1,2 \quad (2)$$

interacting in quadratic-nonlinear media are well known $$\frac{dA_1}{dZ} = \neg \frac{i \cdot 2w^2 - C}{k_1 \cdot \cos^2\alpha_1} \cdot A_2 A_1^* \exp[-i(2k_1 - k_2)Z]; \quad (3)$$

$$\frac{dA_2}{dZ} = \neg \frac{i \cdot 4w^2 C}{K_2 \cdot \cos^2\alpha_2} \cdot A_1^2 \exp[i(2k_1 - K_2)Z],$$

wherein $\bar{e}_j$—wave polarization vectors;
$k_j$—wave vectors;
$A_j$—angle between the wave vector and Pointing vector;

$C = 2\pi/C^2 e_1, \hat{x}(\omega=2\omega-\omega)C_2 C_1 = /2\pi/C^2 e_2 \hat{x}(2\omega=\omega+\omega)e, e,$ —quadratic susceptibility tensor convolutions;
$A_j = \rho_j \exp(i\phi j)$.

This system resolves for conversion in the second frequency doubler. It has been admitted that after doubling in the first doubler and passage of media under investigation, the second doubler of length 1 is hit with radiation having a frequency $\omega$, intensity $J_{\omega 1}$, phase $\phi_1$, and with a frequency $2\omega$, intensity $J_1$, $\phi_2$. Besides this, it has been assumed that $2k_1 - k_2 \approx 0$. Since this is simultaneously a condition for an effective conversion into the second harmonic) and $\cos^2\alpha_j = 1$.

The estimated dependencies of the resulting intensity of the second harmonic rated for the intensity of spurce $J_{\omega 0}$ from the phase difference of interfering waves are given in FIG. 1 and FIG. 2. Here $$I(\psi) = \frac{J(\psi)}{J_{wo}} \; ; J_{wo} = J_{w1} + J_1; I_o = \frac{J_1}{J_{wo}} = 0.01$$

for all the curves in FIG. 1. A variation of dependencies is determined by the parameter $L = 1/l_{nl}, \; l_{nl} = Cn/4\pi l J_{\omega 0}^{1/2}$ i.e., the relation of the radiation intensity of J, length 1 and the non-linear susceptibility $\chi$ of the frequency doubler. For curves 1, 2 (FIG. 1), L=0.5; 1, respectively,—non-linearity slightly affects a kind of dependency $\tau(\psi)$. Considerable changes are observed when L=2, 3, 4, 5 (respectively curves 1, 2, 3, 4, FIG. 2), maximum follow through $\Delta\psi = \pi$, but not $2\pi$ as before maximum standerdized derivative is attained with the other values of $\psi$ (in the figure this point is marked by an arrow) and its value exceeds one.

It follows that the conversion of a radiation source in two successively arranged doublers with the phase media therebetween cannot be seen as an independent conversion in each of them provided that at the input of the second doubler apart from the radiation source, there is non-zero primary radiation propagating along the same path with a frequency and polarization produced in the doubler of the second harmonic.

As distinct from other non-linear interferometers it has own non-linearity even with a linear medium under examination as an interference element is non-linear (second crystal).

Another defect of this type of apparatus resides in spurious pulsations of the phase difference of an interference signal, which appear when an interferometer is illuminated by multimodel radiation and spell the restricted response of the interferometer.

The known device in no way specifies requirements to a radiation source, while the use of a multimodel source brings about the following undesirable consequences:

1. The great pulsations of intensity of a second harmonic with a stable intensity of a source which are due to the phase fluctuations of modes of fundamental radiation.

2. Pulsations of an interference signal phase also associated with the phase fluctuations of source modes.

Note the fact that if the intensity pulsations of the second harmonic can be compensated in detection, spurious phase pulsations cannot be removed this way as being not distinguished from the useful changes of the phase difference. In the event of considerable spurious pulsations an interference pattern is washed off.

ESSENCE OF THE INVENTION

It is the principal object of the present invention to provide a dispersion interferometer with a linear circuit assuring high quality and the explicit interpretation of an interference pattern and accordingly a high accuracy of measurements of dispersion of a refractive index.

Said object is accomplished owing to the fact that in a dispersion interferometer comprising a radiation source with a frequency $\omega$, two nonlinear optical frequency doublers at a distance providing the arrangement of an object under examination between them, light filter and a registering means of the invention, all arranged along an optical axis, provision is made of also a plarization light beam splitter, and two nonlinear optical frequency doublers are so oriented that the directions of polarization of fact waves (with a frequency $2\omega$) are orthogonal with respect to one another and do not coincide with those of said radiation source and light beam splitters.

It is convenient that the frequency doublers and polarization light beam splitter be oriented in such a way that the angles between $e_\omega$ and $Pf^2$ and also $e_\omega$ and $P_f^1$, given the linear polarization of a radiation source, are equal to 45°, wherein $e_\omega$—unit vector of polarization of the radiation source, $P_f^1$ and $P_f^2$—unit vectors of polarization of the fast waves of first and second frequency doublers, $e_c$—unit vector of polarization of radiation passing the light beam splitter. Such an orientation is responsible for a number of advantages of the given alternative embodiment of the device, in particular:

increased contrast range of an interference pattern owing to equalization of the intensity of interfering waves;

the optimum balancing of two recording channels.

According to another modification, the device incorporates a second recording means, and along with this, both recording means are optically connected with the outputs of the polarization light beam splitter. The introduction of the second recording means enables one to realize a circuit of recording with two channels out of phase by $\pi$, which ensures the stability of the interference pattern (or dependency) and also a high reasonse of the interferometer.

In some cases is advisable to use a retro reflector in place of one of the nonlinear optical doublers and additionally introduce a light beam splitter and a phase plate $\lambda/4$ for radiation of double frequency. This embodiment of the interferometer is much simpler, albeit provides a twofold increase of response due to double passage through the object radiated.

In the following alternative embodiment, the radiation source is a mode-locked laser, a factor that removes spurious phase pulsations and permits obtaining a stable interference pattern. Likewise use can be made of a laser source of one or two longitudinal modes.

SUMMARY OF THE DRAWINGS

The invention is explained in greater detail on the examples illustrating the embodiment with the aid of the drawings wherein.

Figure 1:
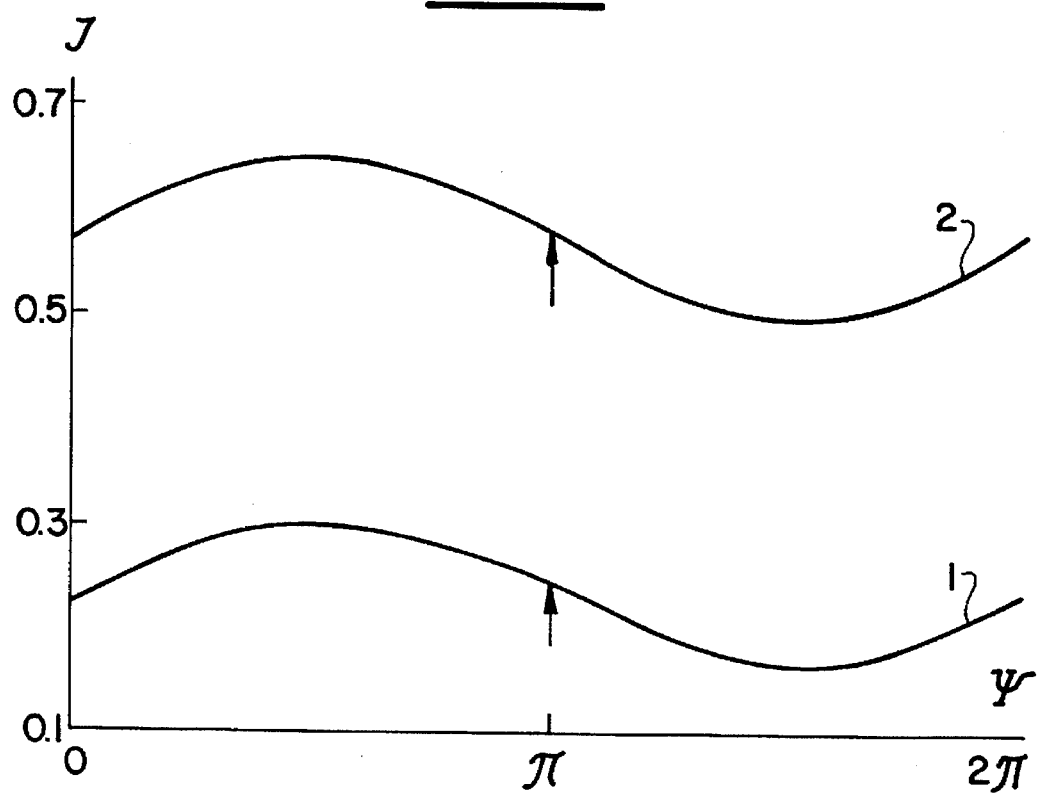
FIG. 1—plot of the resulting dependency of the second harmonic J against the phase difference of interfering waves $\psi$ with the non-linearity parameters of L=0,5;1.
Figure 2:
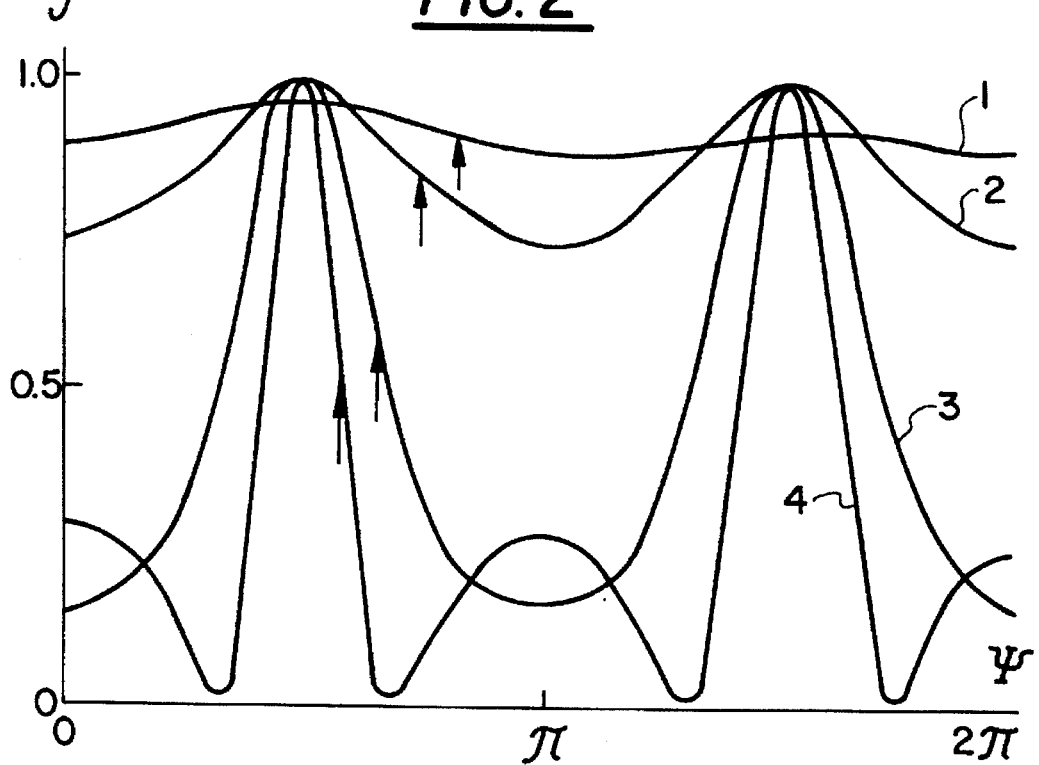
FIG. 2—plot—with the non-linearity parameters of L=2, 3, 4, 5.
Figure 3:
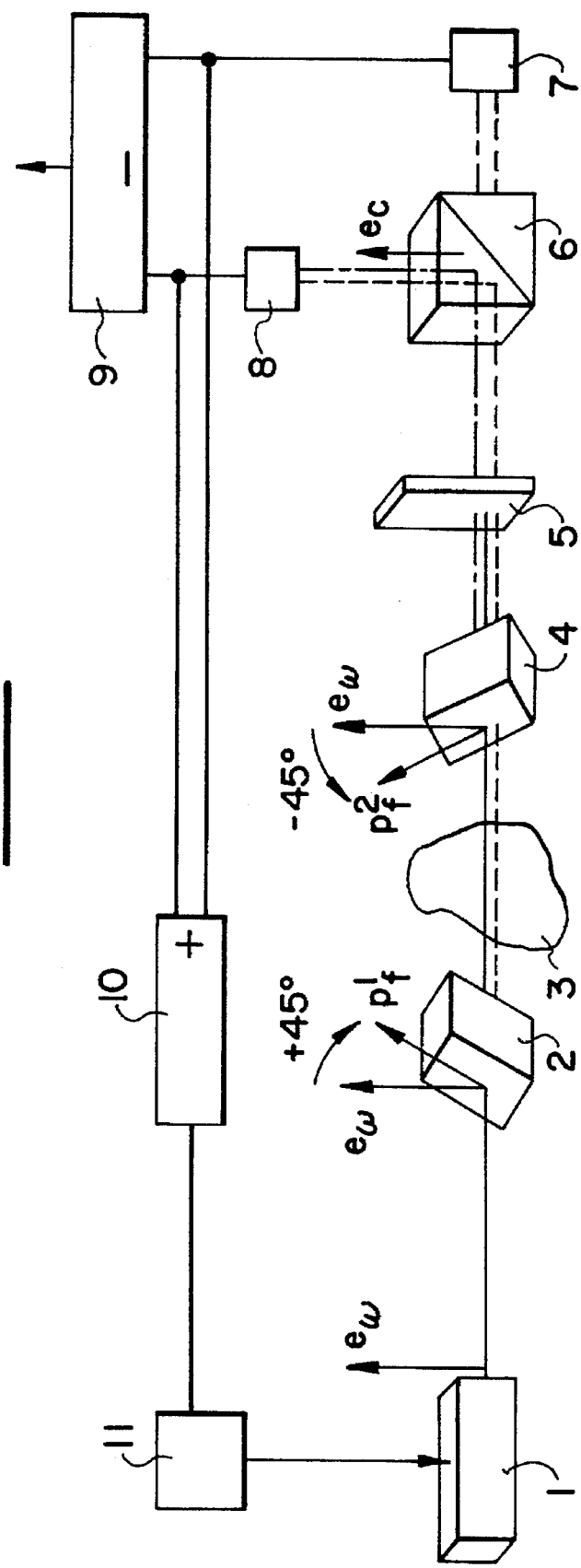
FIG. 3—basic circuit of a dispersion interferometer.

The circuit of a dispersion interferometer comprises a radiation source 1, a first non-linear optical doubler of frequency 2, subsequent to which is installed an object 3 under investigation, a second non-linear optical frequency doubler 4, a light filter 5, a polarization beam splitter 6, recording devices 7, 8, a differential amplifier 9, an adder 10, a control element 11 signal conditioner (FIG. 3). Shown further is an element orientation where $P_f^1$ and $P_f^2$—direction of fast wave polarization in the first and second doublers, $e_\omega$—unit polarization vector of the source. By the optical frequency doubler is implied an element so made that the second harmonic of probing radiation is produced in the most favourable way, said radiation passing through the doubler in a direction of phase-matching without a marked shift and change of polarization. In anisotropic media radiation is resolved into two waves: fast and slow with mutually orthogonal polarization Pf⊥Ps. The refractive indices of media for fast $n_f$ and slow ns waves meet the condition of $n_f < n_s$. The directions of Pf and Ps are uniformly associated with the axes of the crystal. Specifying the "mutually orthogonal" orientation of non-linear elements and introducing a linear interference element in the form of a polarization beam splitter permits obtaining an interference pattern for which the dependence of intensity of the second harmonic on the dispersion phase difference is as follows (1):

$$J = J_1 + J_2 + 2\sqrt{J_1 J_2} \cos\psi$$

and it does not alter with any power of said probing radiation and non-linear element lengths. This occurs owing to the fact that doubling of the frequency in the second non-linear element does not depend on the second harmonic produced by the first non-linear element.

The technical solution as claimed is a case when a system of two non-linear elements can be regarded as a linear dispersion interferometer, i.e. transformation proceeds independently in each of the elements.

Figure 4:
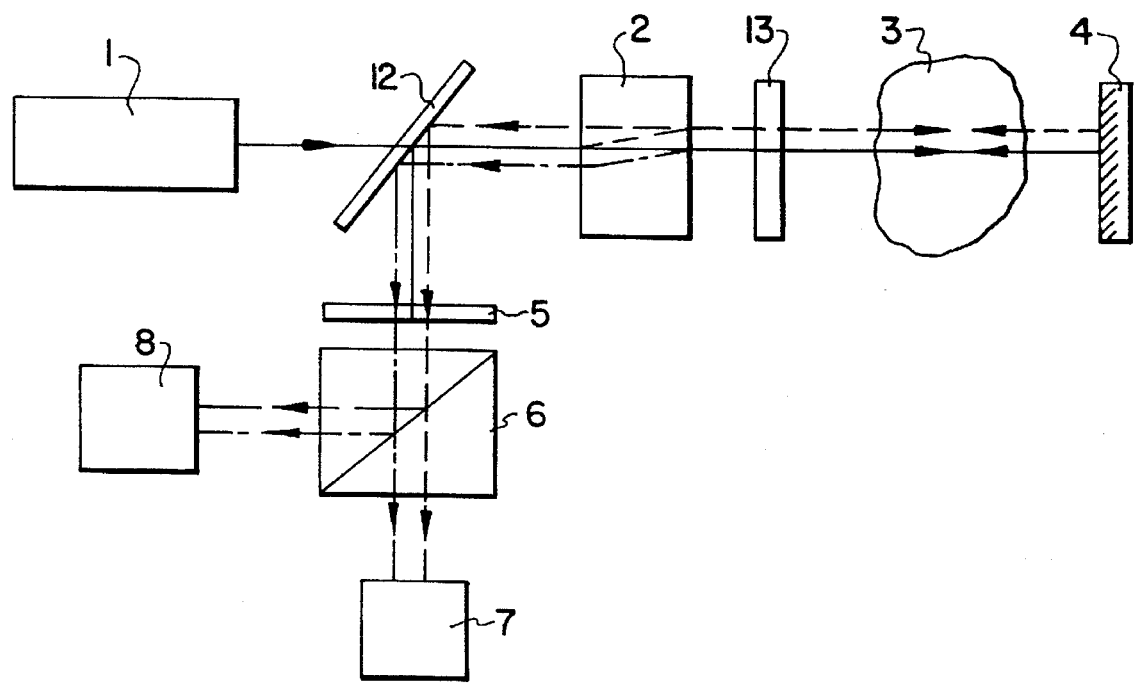
FIG. 4—another alternative embodiment of a dispersion interferometer circuit.

FIG. 4 illustrates a diagram of the autocollimation variant of a linear dispersion interferometer. Said diagram includes the radiation source 1, a beam splitter 6, the optical frequency doubler 2, a phase plate 13, the investigated object 3 a retro-reflector 14, the light filter 5, a polarization beam splitter, and recording devices 7, 8.

Operation of an apparatus (FIG. 3) is carried out in the following manner.

On illuminating an interferometer with laser radiation with a frequency $\omega$ and polarization $e_\omega$ forming the angle of 45° with $Pf^1$, part of this radiation is converted into harmonic radiation with a frequency $2\omega$ and a polarization vector $e_{2\omega}^{(1)} \| P_f^1$ in the first nonlinear element. Thus, the object under examination is rayed with two waves having the frequencies $\omega$ and $2\omega$. On passing through the second nonlinear element 6 oriented right-angled to the first, i.e. $Pf^1 \perp Pf^2$, the probing radiation is again converted into a harmonic wave woth the frequency $2\omega$ and polarization $e_{2\omega}^{(2)} \perp e_{2\omega}^{(1)}$. The conversion process does not depend on the harmonic produced by the first nonlinear element because $e_{2\omega}^{(1)} \perp P_f^2$. Light filter 5 cuts off the radiation of the basic frequency. There remain two $2\omega$ waves polarized orthogonally, of which one has been converted before passage through the object, and the other—thereafter. Each of the waves is divided by a polarization light beam splitter into components $e_c$ and $e_{c1}$ oriented at 45° to $e_{2\omega}^{(1)}$ and $e_{2\omega}^{(2)}$. A part of the wave (with polarization $e_c$) is directed by the splitter to a photodetector 8 and the other part ($e_{c1}$)—a photo detector 7. Thus, in each beam after the splitter 6 one can observe the interference of projections of two waves originated by doublers 2 and 4. Inasmuch as mutually orthogonal polarizations correlate to the given beams, the interference signal of the photodetector 7 is out of phase with respect to the signal of photodetector by $\pi$. Thus, the signals from the photodetectors are as follows:

$$S \sim \frac{1}{2} I_1 + \frac{1}{2} I_2 + \sqrt{I_1 \cdot I_2} \cdot \cos\psi$$

$$S_1 \sim \frac{1}{2} I_1 + \frac{1}{2} I_2 - \sqrt{I_1 \cdot I_2} \cdot \cos\psi$$

In a difference signal from the differential amplifier 9 we have:

$$\Delta S = S - S_1 \sim 2\sqrt{I_1 \cdot I_2} \cdot \cos\psi$$

On measuring the phase shifts less and far less than $\pi$, it is expedient to make measurements on the linear portion of dependency $\Delta S(\psi)$ near the "middle point" $\psi = \pi/2$. The restoration of the middle point and calibration, i.e. the definition of value $2\sqrt{I_1 I_2}$ is generally made through use of an optical wedge interposed between the frequency doublers.

Note also the fact that in the difference signal are compensated steady components of interference signals together with pulsations. For stabilizing the dependence $\Delta S(\psi)$, normalization is applied to the total signal $S+S\perp \sim I_1+I_2$, which is not dependent on the phase difference measured. Another method of stabilization resides in providing a feedback loop comprising the adder 10, the control element II signal conditioner and an element monitoring laser radiation intensity.

An important circumstance is that the laser operates in the conditions of mode-locked when the phase ratio of various modes is fixed (or single-, two-mode conditions when the phase pulsations of a source do not show up). But here no spurious phase pulsations are present and compensation and stabilizing methods of registration are possible.

The vector of polarization of probe radiation $e_\omega$ shouldn't coincide with $P_f^{1,2}$ and $P_s^{1,2}$. Inasmuch as the maximum contrast of an interference pattern is achieved with the equal intensities of interference waves, the optimum angle between $e_\omega$ and $e_{2\omega}^{(1)}(e_{2\omega}^{(1)}$ coincides with $P_f^1$ is 45°. For conversion into the second harmonic at type 11 phase-matching, the angle of 45° is a most favourable one for effective conversion.

According to the autocollimation variant of FIG. 4, the radiation of a source with a frequency $\omega$ and a polarization $e_\omega$ is converted into that of a harmonic with frequency $2\omega$ and $\chi$ a polarization $e_{2\omega} \| P_f$ in the frequency doubler 2. After forward and backward passage through a plate $\lambda/4$ 13 and the object under examination 3, the radiation polarization of the second harmonic revolves through 90°. i.e. $\perp P_f$. Thus, doubling of the frequency of basic radiation in backward passage occurs regardless of one produced in a straight direction and the polarization of two waves with the frequency $2\omega$ are mutually orthogonal. The phase plate is selected such that radiation polarization with the frequency $\omega$ is not altered. When the angle between $e_\omega$ and $P_f$ is 45° this is done automatically. A semitransparent mirror 12 directs the radiation to a polarization beam splitter and a registering circuit. The retro-reflector 14 is either a mirror or a corner reflector.

It follows from the above that conversion of probing radiation into the second harmonic occurs in orthogonal polarizations and therefore independently in both non-linear elements. Moreover the interference elements (its function is performed by a polarization beam splitter) is a linear one, in which case a period of an interference pattern is always $2\pi$ and the normalized maximum derivative $I'_{max\ (\psi)}/(I_{max}-I_{min})$ is always I regardless of the length and non-linear susceptibility of elements and power density of the probing radiation.

It is necessary to additionally note the technical and economic advantages of the given device over prior art. There follows from the specification that registered are two interference patterns in mutually orthogonal polarizations and are out of phase with respect to each other by $\pi$, i.e. $Ic(\psi)=Ic\perp(\psi+\pi)$. In photoelectric recording, this circumstance enables one to compensate the power instability of probing radiation without expenditure, using the difference signal between a direct and a perpendicular channel. This is conductive to a high sensitivity of measurements—better than the 10–3 interference band.

INDUSTRIAL APPLICABILITY

The interferometer under examination can be used in distant measurement systems and accurate travel meters.

We claim:

1. An interferometer comprising:

a radiation source having a polarization axis, a first non-linear optical frequency doubler having a first optical axis and a first polarization direction of fast waves, said first polarization direction differing from said polarization axis of the radiation source, a second non-linear optical frequency doubler having a second optical axis located longitudinally with respect to said first optical axis and having a second polarization direction of fast waves, said second polarization direction of fast waves being orthogonal to said first polarization direction of fast waves and differing from said polarization axis of the radiation source, said second non-linear optical frequency doubler being located at a distance from said first non-linear optical frequency doubler for securing an investigated object, a light filter having an optical axis located longitudinally with respect to said first and said second optical axes, a polarization beam splitter having an optical axis located longitudinally with respect to said optical axis of said light filter, having a polarization direction which differs from said first polarization direction and from said second polarization direction, and having first and second optical outputs, and a recording device which is optically coupled with said first output of said polarization beam splitter.

2. An interferometer as claimed in claim 1, wherein an angle between a unit vector $e_c$ of two orthogonal polarization directions of said polarization beam splitter and a unit vector $P_f^{(2)}$ of polarization of the fast waves of said second non-linear optical frequency doubler is equal to an angle between a unit vector $e\omega$ of polarization of said radiation source and a unit vector $P_f^{(1)}$ of polarization of the fast waves of said first non-linear optical frequency doubler and is equal to 45 grad.

3. An interferometer as claimed in claim 1, and further comprising a second recording device, wherein said first recording device and said second recording device are optically coupled with the outputs of said polarization beam splitter.

4. An interferometer as claimed in claim 3, in which the radiation source used is a mode-locked laser.

5. An interferometer as claimed in claim 3, in which the radiation source is a laser of one or two longitudinal lazing modes.

6. A dispersion interferometer based on generation of two orthogonally polarized waves of a second harmonic, comprising:

a radiation source having a first optical axis and a polarization axis, an optical frequency doubler having an optical axis located longitudinally with respect to said optical axis of the radiation source and having a polarization direction of fast waves, said polarization direction differing from said polarization axis of the radiation source, a retro-reflector having an optical axis located longitudinally with respect to said optical axis of said radiation source, said retro-reflector being located at a distance from said optical frequency doubler for securing an investigated object, a phase plate having a phase shift of L/4 for radiation of a double frequency and located between said optical frequency doubler and said investigated object, a beam splitter located between said radiation source and said optical frequency doubler, said beam splitter being used for transmitting and reflecting a beam from said radiation source and reflecting a beam of double frequency from said optical frequency doubler in a direction which is orthogonal to said first optical axis and forms a second optical axis, a light filter having an optical axis located longitudinally with respect to said second optical axis;

a polarization beam splitter having an optical axis located longitudinally with respect to said second optical axis and having a polarization direction which differs from said polarization axis and from said polarization direction of said optical frequency doubler, said polarization beam splitter having a first output and a second output, and first and second recording devices which are optically coupled with said first and second outputs of said polarization beam splitter.

\* \* \* \* \*